(12) United States Patent
Becker

(10) Patent No.: US 10,016,872 B2
(45) Date of Patent: Jul. 10, 2018

(54) METHOD FOR PRODUCING A MIRROR SUBSTRATE BLANK OF TITANIUM-DOPED SILICA GLASS FOR EUV LITHOGRAPHY, AND SYSTEM FOR DETERMINING THE POSITION OF DEFECTS IN A BLANK

(71) Applicant: Heraeus Quarzglas GmbH & Co. KG, Hanau (DE)

(72) Inventor: Klaus Becker, Hanau (DE)

(73) Assignee: Heraeus Quarzglas GmbH & Co. KG, Hanau (DE)

( * ) Notice: Subject to any disclaimer, the term of this patent is extended or adjusted under 35 U.S.C. 154(b) by 0 days.

(21) Appl. No.: 14/903,799

(22) PCT Filed: Jul. 2, 2014

(86) PCT No.: PCT/EP2014/064036
§ 371 (c)(1),
(2) Date: Jan. 8, 2016

(87) PCT Pub. No.: WO2015/003966
PCT Pub. Date: Jan. 15, 2015

(65) Prior Publication Data
US 2016/0151880 A1 Jun. 2, 2016

(30) Foreign Application Priority Data
Jul. 9, 2013 (DE) .......... 10 2013 107 215

(51) Int. Cl.
*B24B 49/12* (2006.01)
*G01N 21/958* (2006.01)
(Continued)

(52) U.S. Cl.
CPC .............. *B24B 49/12* (2013.01); *B24B 7/241* (2013.01); *B24B 13/0018* (2013.01);
(Continued)

(58) Field of Classification Search
CPC .... B24B 49/12; B24B 49/10; G01N 21/8851; G01N 21/985; G01N 2021/8861; G01N 2201/06113
(Continued)

(56) References Cited

U.S. PATENT DOCUMENTS 3,814,946 A 6/1974 Takahashi et al.
5,196,716 A * 3/1993 Moriya ............. G01N 21/9505
250/559.16
(Continued)

FOREIGN PATENT DOCUMENTS

DE 69307722 T2 6/1997
DE 10210209 A1 9/2003
(Continued)

OTHER PUBLICATIONS

International Preliminary Report on Patentability dated Jan. 21, 2016 in International Application No. PCT/EP2014/064036.
(Continued)

*Primary Examiner* — Robert Rose
(74) *Attorney, Agent, or Firm* — Panitch Schwarze Belisario & Nadel LLP

(57) ABSTRACT

A method for producing a mirror substrate blank made from titanium-doped silica glass for EUV lithography, having a thickness of at least 40 millimeters, includes steps of face grinding the surface of the blank and identifying data on defects in a surface layer of the blank. Light penetrates the blank at a predetermined angle of incidence $\alpha$ of less than 90° at a location on the flat surface of the blank. The light scatters on a defect in the blank, and the scattered light is detected at a distance x from the penetration location on the surface of the blank by a light detection element arranged perpendicularly thereabove. The method further includes steps of determining the position of the defect in the surface
(Continued)

layer based on the obtained data, and partial or complete removal of the surface layer in consideration of the position determination and forming the mirror substrate blank.

10 Claims, 2 Drawing Sheets

(51) Int. Cl.
    *B24B 13/00* (2006.01)
    *B24B 7/24* (2006.01)
    *G01N 21/88* (2006.01)
    *G01N 21/896* (2006.01)

(52) U.S. Cl.
    CPC ....... *G01N 21/8851* (2013.01); *G01N 21/958* (2013.01); *G01N 2021/8861* (2013.01); *G01N 2021/8967* (2013.01); *G01N 2201/06113* (2013.01)

(58) Field of Classification Search
    USPC .................................... 451/41, 42, 6, 7, 5
    See application file for complete search history.

(56) References Cited

U.S. PATENT DOCUMENTS

| | | | |
|---|---|---|---|
| 5,598,262 A | 1/1997 | Jutard et al. | |
| 6,542,849 B2 * | 4/2003 | Sun .................. | G01B 11/06 |
| | | | 702/170 |
| 2006/0001885 A1 | 1/2006 | Hertzsch et al. | |
| 2007/0096044 A1 | 5/2007 | Johannesson et al. | |
| 2011/0090492 A1 | 4/2011 | Lemke et al. | |

FOREIGN PATENT DOCUMENTS

| | | |
|---|---|---|
| DE | 102004017237 A1 | 11/2005 |
| DE | 102009043001 A1 | 4/2011 |
| DE | 102011087460 B3 | 6/2013 |
| JP | H02116704 A | 5/1990 |
| WO | 0118532 A1 | 3/2001 |
| WO | 2006108137 A2 | 10/2006 |

OTHER PUBLICATIONS

International Search Report dated Sep. 24, 2014 in International Application No. PCT/EP2014/064036.
Office Action dated Mar. 24, 2014 in DE Application No. 102013107215.1.

\* cited by examiner

Prior art

METHOD FOR PRODUCING A MIRROR SUBSTRATE BLANK OF TITANIUM-DOPED SILICA GLASS FOR EUV LITHOGRAPHY, AND SYSTEM FOR DETERMINING THE POSITION OF DEFECTS IN A BLANK

CROSS-REFERENCE TO RELATED APPLICATIONS

This application is a Section 371 of International Application No. PCT/EP2014/064036, filed Jul. 2, 2014, which was published in the German language on Jan. 15, 2015, under International Publication No. WO 2015/003966 A1 and the disclosure of which is incorporated herein by reference.

BACKGROUND OF THE INVENTION

The present invention refers to a method for producing a mirror substrate blank of titanium-doped silica glass for EUV lithography with a thickness of at least 40 millimeters.

Furthermore, the present invention refers to a system for determining the position of defects in a mirror substrate blank of titanium-doped silica glass for EUV lithography.

EUV (Extreme Ultra Violet) lithography requires a material with no noticeable thermal expansion in the temperature range between 20° C. and 40° C. for mask and mirror substrates. Glass with a high silicic-acid content that is doped with titanium oxide, hereinafter called Ti-doped silica glass, meets these conditions. Doping with titanium oxide, however, yields a brownish coloration of the glass. The shaped articles for this kind of application, hereinafter also called blanks, are large, thick, dark-brown plates with dimensions of up to about 70×60×20 cm$^3$, which after corresponding grinding, polishing and measuring operations, are further processed, for instance, into reflective mirrors.

What has turned out to pose problems is that, due to the manufacturing process, defects may occur in the form of bubbles or inclusions in near-surface regions of the blanks and that during polishing, these may rise to the surface of a mirror geometry and may impair the imaging quality of the mirror or mask blanks. The localization of possible defects of the blank prior to polishing is therefore a basic demand made by optics manufacturers for EUV lithography devices.

Optical measurement methods for detecting defects in the interior of glasses are normally based on an assembly in which light impinges in a vertical direction on a glass sheet and the light scattered on the defects is detected in vertical direction relative to the illumination direction. A schematic illustration of this is shown in FIG. 1b. It is thereby possible to determine the exact position of the defect point, either a bubble or an inclusion, at a distance from the surface of the glass. This measurement method is well suited for transparent glasses, but is not expedient for colored glasses that show a high light absorption. Moreover, even for transparent glasses, a limiting factor is the sample size because the light intensity (i.e., also that of the scattered light) is considerably decreasing with the path length, so that the image of a defect is no longer visible to an observer, starting from a distance defined by the lateral extension of the glass sheet. Defects located in the center of the glass sheet, i.e., at a great lateral distance from the observation position, are not accurately detected or are not detected at all.

Furthermore, it is known that defects are detected with respect to their position on the surface of opaque or semi-transparent material in that a laser light is directed at an angle relative to the surface to be analyzed and the scattered light reflected by the defect is sensed by a photosensor while the material sample is moved in a controlled manner in a horizontal plane. This measurement arrangement is known, for example, from JP 02-116704. It is, however, not suited for detecting defects in the interior of the material sample and for determining the depth thereof.

WO 2006/108137 A2 suggests various systems for detecting defects in or on very thin transparent glass material for liquid crystal displays (LCD). Such glass sheets have a thickness in the range of less than one millimeter to not more than about two millimeters. The large-area glass material is passed underneath a measurement system, wherein according to one variant, the total reflection on the internal boundary surfaces of the thin glass sheet of a laser beam penetrating at an angle relative to the surface is used for detecting defects. An internally located defect generates scattered light whenever it is detected by the laser beam, which is "indirect" due to total reflection. A camera arranged at a distance from the laser light source receives this scattered light and can determine the position of the defect in horizontal direction (x/y-direction), but not in the depth (z-direction) of the thin glass sheet.

According to another variant shown in WO 2006/108137 A2, defects can be detected on both surfaces or in the interior of the thin glass sheet with respect to their position by employing the parallax shift principle with two lasers and two detectors, between which an angle is set. In consideration of the running-time measurement of the moved glass sheet, the position of the defect can also be derived within the glass sample. The measurement arrangement is complicated because one needs two respective lasers and detectors. Moreover, an exact detection of the movement speed is required for the evaluation.

DE 10 2011 087 460 B3 discloses a method for detecting defect points in a transparent body with an undefined complex surface, which method is particularly employed for checking sapphire crystals. The light irradiated into the transparent body is scattered on defect points and on the complex surface. With the help of camera systems, a series of images are recorded at several emission points of the light. As in the case of computer tomography, the course of the injected light can be reconstructed therefrom. Defect-free areas in the test pieces (sapphire crystals) can thus be identified.

According to DE 10 2009 043 001 A1, the size and shape of a defect in a transparent material can be determined, and a light beam is here incident on the specimen at the entrance area, and it runs through the specimen and is scattered on a defect. An angle-resolved measurement of scattered light caused by defects is taken at the exit area. The method is only suited for fully transparent material. Another complicated optical imaging system is required for determining the depth positions of the defects.

Similar to DE 10 2009 043 001 A1, a measured value regarding the optical quality of a transparent material is also obtained in the method according to DE 10 2004 017 237 A1.

Finally, DE 693 07 722 T2 discloses a method and an apparatus for determining defects in glasses, particularly bubbles. The measurement set-up is based on the visualization of the defects through the transparent material by image generation in the three dimensions X, Y and Z.

The standard measurement methods for localizing defects in glass material are either geared for detection on the surface, or in a very small depth range underneath the surfaces, or—as far as the matrix area is of interest—for transparent glass. In EUV lithography, however, large optics of Ti-doped silica glass are used, for the production and qualification of which the measurement methods for localizing defects in the glass material according to the prior art are inadequate.

BRIEF SUMMARY OF THE INVENTION

It is therefore an objective of the present invention to provide a method for producing a mirror substrate blank of Ti-doped silica glass for EUV lithography which, in terms of the qualification of the blanks with respect to the localization of defects, is optimized for the further processing steps.

The method for producing a mirror substrate blank of titanium-doped silica glass for EUV lithography with a thickness of at least 40 millimeters, according to the present invention, comprises the following method steps:
  a) face grinding the surface of the blank;
  b) determining data on defects in a surface layer of the blank, wherein
     b1) light penetrates at a place of the flat surface of the blank at a predetermined angle of incidence α of less than 90° into the blank,
     b2) the light is scattered on a defect in the blank, and
     b3) the scattered light is detected at a distance x from the penetration point on the surface of the blank by a light detection element which is vertically arranged thereabove;
  c) determining the position of the defect in the surface layer on the basis of the data obtained in method step b); and
  d) partly or fully removing the surface layer in consideration of the determination of the position according to method step c) and with formation of the mirror substrate blank.

Furthermore, it is an objective of the present invention to provide a system for determining the position of defects in mirror substrate blanks of titanium-doped silica glass for EUV lithography which, in the method according to the present invention, allows for a simple, but nevertheless exact, determination of the position of defects in the blank.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1A:
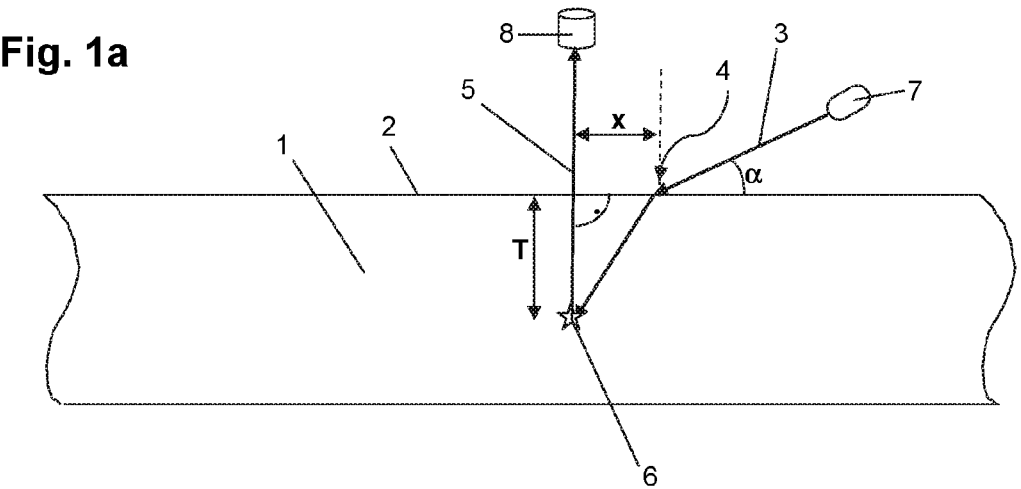
FIG. 1a is a schematic illustration of the system according to an embodiment of the present invention.
Figure 1B:
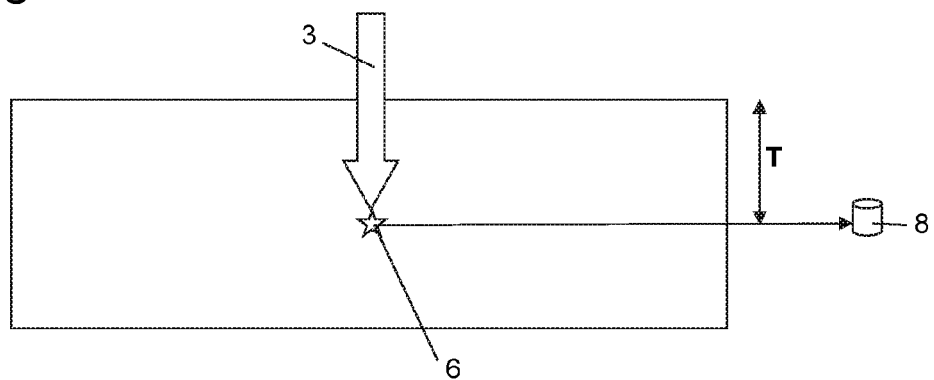
FIG. 1b is a schematic illustration of a system for detecting defects in glasses according to the prior art.

In the method according to the present invention, the starting material for the mirror substrate blank is a Ti-doped silica glass mass which is shaped into a plate-shaped blank with typical dimensions of 50×40×15 cm$^3$ and which is free of streaks and striae in all of the three viewing directions. As a rule, it can be assumed that a homogeneous low-bubble material is produced during fusion and shaping of the Ti-doped silica glass blank, which material meets the requirements of bubble class 0 according to DIN 58927 2/70. This standard specifies the following: the sum of the cross-sections of all bubbles of a piece based on 100 cm$^3$ of its volume is 0.03 mm$^2$; bubbles and inclusions with a diameter of <0.08 mm are not taken into account. Bubbles outside of the range intended for concave mirror grinding are, in general, accepted. This range has a typical thickness of a few millimeters, but can also extend into the mirror substrate blank up to a depth of 50 mm.

Precise data on the position of defects in a surface layer of such a blank are needed for the production of a mirror substrate blank. This allows for a fine positioning of the mirror surface, so that no bubbles come to rest on the final surface. To this end, the surface of the plate-shaped blank is, first of all, face ground. Subsequently, the data on defects in a surface layer of the non-transparent, brown-colored blank are determined with the following method steps: light in the form of a focused light beam penetrates at a place of the substantially flat surface of the blank at a predetermined angle of incidence α of less than 90° into the blank. The angle of incidence α designates the angle between the light beam and the surface of the blank as horizontal. At the point of penetration (defined as zero point), the light is deflected into the volume of the blank according to the refractive index of the Ti-doped silica glass, and scattered light that at a distance x from the point of entrance of the light beam reaches the surface is produced upon impingement on a defect point in the form of a bubble or inclusion. The scattered light is here detected by a light detection element that is arranged at a right angle above the surface of the blank. To determine the position of the defect in the surface layer on the basis of the data acquired, the following formula is used for the depth T at which the bubble is positioned underneath the surface:

$$T=x/(\tan(\arcsin(\sin(90-\alpha)/n))$$

The refractive index n for silica glass doped with 8 wt. % TiO$_2$ is 1.48.

After the position of a bubble has been determined in this way, the surface layer is removed by further grinding, so that no bubbles will be located on the surface in the subsequent final polishing operation for forming a mirror surface, which is concave as a rule. Possible bubbles in the near-surface area are thus eliminated by the partial or complete removal of the surface layer. If, in the individual case, defects in the form of bubbles or inclusions are not detected in the relevant area of the surface layer, a surface layer need not be removed. Likewise, it may be that in the individual case that the detected defects are positioned so close to the surface that they will be eliminated without any difficulty in the final mirror-grinding step, whereby removal of the affected surface layer of the blank according to method step d) can be dispensed with. With the help of the position determination of the defects in the Ti-doped silica glass blank, the mirror substrate blank is reliably qualified as an intermediate product before the complicated processing step for producing the mirror surface is carried out. This optimizes the manufacturing method for mirror substrate blanks of Ti-doped silica glass for use in EUV lithography.

In the simplest case, the collection of data on defects and the determination of the position of the defects in the surface layer can be carried out by an observer directly reading the position of the bubble in the horizontal plane with the help of a scale arranged on the surface of the blank.

It has been found that the method according to the present invention can be carried out in a particularly simple manner if the angle of incidence α at which the light is incident on the flat surface of the blank is set to range from 5° to 75°. A positioning of the incident light in this range of angle offers enough handling space for the measurement set-up. At small angles, the point of exit of the scattered light is relatively far away from the penetration point, resulting in a reduced intensity of the scattered light. The determination of the position, especially of bubbles that are located deeper in the surface layer, is thus difficult and inaccurate. In the case of a light source arranged at a steep angle above the surface of the blank, i.e., at angles of more than 75°, the penetration point of the light beam and the exit point of the scattered light are relatively close to each other. This is detrimental to the measurement and causes errors.

Laser light is preferably used as incident light for the method according to the present invention. Since laser light is available at specific selectable wavelengths (colors), the corresponding laser light can optimally be selected with respect to brilliance for the measurement situation and the blank.

Preferably, laser light is produced with a line focus, and a laser with a rated power of at least 1 mW is used for producing the laser light. The line focus transforms the initially spot-like laser light beam into a line of parallel laser light. With this laser line, an area that is larger by comparison with the spot-like illumination is detected in the surface layer of the Ti-doped silica glass blank, which accelerates the method step for determining data on defects in the Ti-doped silica blank. The rated power of the laser light is typically in the range of 5 to 50 mW. A laser light with a rated power of considerably less than 1 mW is too weak, and therefore not suited for detecting defects in the blank. A rated power of little more than one milliwatt is, however, enough for the inventive application. Such a laser light is cost-effective in terms of purchase and has a long service life of more than 10,000 hours. On the other hand, the rated power of the laser light should not be much higher than 50 mW because this would require an operation of enhanced laser protection.

For an efficient performance of the method, a laser is selected which emits in the wavelength range of 500 nm to 1500 nm. This wavelength range is advantageous because a visual detection is possible and also the use of an infrared sensor as a light detection element for automatically detecting the scattered light. The Ti-doped silica glass, in particular, shows high transparence in the infrared range, so that laser light of a corresponding wavelength is advantageous.

In principle, it may also be advantageous to use several spaced-apart laser light sources with different wavelength ranges that detect surface layer regions of different depths. The method according to the present invention is thereby made even more efficient.

A further optimization with respect to the method step for determining data on defects in a surface layer of the blank is that the light detection element for detecting the scattered light emanating from the defect in the blank is part of a camera system with an evaluation unit. The scattered light emanating from the defect in the glass blank is detected with the light detection element of the camera system and converted into a signal. Due to the arithmetical processing of the signal in the evaluation unit, the spatial position of the defect is determined in the blank. It is further possible to connect the camera system to an imaging device in addition, so that apart from the position data of the defect as arithmetical coordinates, determined via the evaluation unit, it is also possible to obtain a distribution image of the defects in the surface layers of the blank.

It has turned out to be useful to select the camera system such that the intensity of the scattered light is also detected and the magnitude of the defect is determined arithmetically therefrom in the evaluation unit. This variant is advantageous when specific minimum or maximum values of defects are specified that limit the further processing into a mirror substrate blank for EUV lithography.

With respect to a particularly fast and economic procedure, it has been found to be advantageous that the penetration point of the light and the light detection element are guided in a grid-like manner over the face ground surface of the blank. The surface of the blank is here scanned over a large area with the incident light and the light detection element, wherein the horizontal coordinates of the light penetration point and, derived therefrom, also those of the detected defects are recorded as well as the depth position of the defect determined via the light detection element. This type of grid-like guidance of the light penetration point together with the light detection element over the surface of the blank can be automated easily. As a rule, the blank can also be moved. Since the weight of the blanks with 50-80 kg is, however, relatively great, it is easier to move, inversely, the light penetration point and the light detection element. Preferably, the movement is carried out by way of a fixed incidence angle adjustment and a preset position for the light detection element that conforms to the distance x between the penetration point of the light and the exit point of the scattered light. When the joint grid-like guidance of penetration point and light detection element over the same surface section of the blank is repeated, the position of the light detection element is changed, so that different depth sections of the surface layer of the blank are progressively detected.

Furthermore, it has turned out to be advantageous to wet the face ground blank over the whole surface with immersion oil prior to the determination of data on defects according to method step b). To determine the position of the defects in the surface layer of the Ti-doped silica glass blank, the surface is first of all face-ground. The grinding efforts can be minimized if, after a first grinding operation, the plate-shaped blank is wetted with immersion oil over the whole surface. The surface of the blank is sufficiently prepared by way of this measure for the determination of data regarding the defects in the blank.

As for the system for determining the position of defects in a mirror substrate blank of Ti-doped silica glass for EUV lithography with a thickness of at least 40 millimeters in the method according to the present invention, the above-mentioned objective starting from a light source for generating light and a light detection element for detecting scattered light is achieved according to the present invention, in that the light source is arranged relative to the blank such that light penetrates at a predetermined angle of incidence α of less than 90° into a face ground surface of the blank, the light is scattered on a defect in the blank, the light detection element is arranged such that it detects the scattered light exiting at a distance x from the penetration point, vertically above the surface of the blank, and an evaluation unit determines the position of the defect on the basis of the data detected by the light detection element.

The system according to the present invention for determining the position of defects in a surface layer of the brown-colored low-transmission blank of Ti-doped silica glass is characterized in that an illumination source is arranged such that the light penetrates at a place of the substantially flat surface of the blank at a predetermined angle of incidence α of less than 90° into the blank. The angle of incidence α designates the angle between the light beam and the surface of the blank as horizontal. At the penetration point the light is deflected into the volume of the blank according to the refractive index of the Ti-doped silica glass, and scattered light is produced upon impingement on a defect point in the form of a bubble or an inclusion. The scattered light exits at a distance x from the penetration point (defined as zero point) from the surface and is detected by the light detection element arranged at a right angle above the surface of the blank. The following formula is used for determining the position of the defect in the surface layer on the basis of the acquired data with respect to the depth T at which the defect, for instance in the form of a bubble, is positioned underneath the surface:

$$T=x/(\tan(\arcsin(\sin(90-\alpha)/n))).$$

The refractive index n for silica glass doped with 8 wt. % $TiO_2$ is 1.48 and is inserted into the calculation formula in a corresponding manner.

Hence, the system according to the present invention permits a simple, but nevertheless exact, determination of the position of defects (bubbles or inclusions) in the matrix of low-transmission glass, e.g. in the Ti-doped silica glass blank. The system is independent of the size of the sample in the area, because the detecting process is carried out and directed only from above onto the face ground surface. In this respect, the system is suited for low-transmission glasses and colored glass blanks of Ti-doped silica glass and also for large-volume transparent glass samples in which the scattered light cannot be detected in a direction perpendicular to the incident light; i.e., by lateral viewing of the sample. The system is thus particularly suited for mirror substrate blanks and also for mask plates for EUV lithography.

EXAMPLE 1

A silica glass blank 1 doped with 8 wt. % $TiO_2$ in cylinder geometry with a diameter of 381 mm (~15 inches) and a thickness of 100 mm is face ground on the surface 2 and then view-polished. Thereafter, the surface 2 shows a mean roughness Ra of about 1 nm. The position data of defects 6 found in this blank 1 (e.g., bubbles) are determined by arranging a light 3 in the form of a laser light at an angle of incidence α of 25° on the face ground and polished surface 2 of the blank 1. For this purpose, a standard laser pointer is adequate as a light source 7. The laser pointer has a rated power of 5 mW and emits green light 3 with a wavelength of 532 nm. At the place where the laser light 3 penetrates into the Ti-doped silica glass blank 1, a scale is placed on the surface of the blank, namely in such a way that it coincides with its ruler edge at the point of penetration 4 of the laser light as zero point. The scattered light 5 is visually detected, with the scattered light 5 being observed at a distance x from the penetration point 4 of the laser light 3 vertically above the ruler edge. The depth position T of the bubble is calculated from the formula: $T=x/(\tan(\arcsin(\sin(90-\alpha)/n)))$. The data obtained thereby on the position of the bubbles 6 in horizontal direction and in depth direction T are recorded. Three defects 6 in the form of bubbles are found in the blank 1 and their position data are recorded in Table 1. A bubble defect 6 is found at a depth of 3 millimeters; the two other defects are positioned at a depth of 18 mm and 21 mm, respectively, underneath the surface 2 of the blank 1. It seems that the bubbles 6 have a diameter of more than 100 µm.

Figures 2A, 2B:
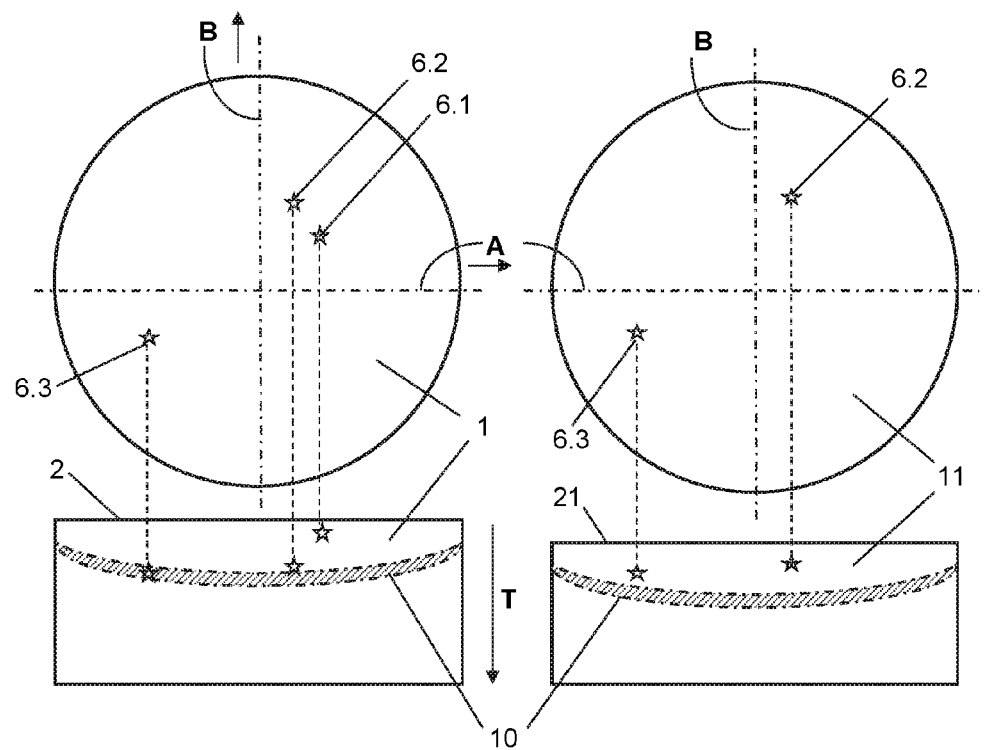
FIGS. 2a and 2b each show a bubble distribution diagram in a top view and in a side view of the mirror substrate blank according to Example 1, before and after removal of a surface layer.

FIG. 2a shows the positions of the determined bubble defects 6.1, 6.2, 6.3 in a top view on the blank 1 on the basis of the coordinate axes A and B, and in a side view in the direction of depth T. A concave mirror surface 10 is provided for the mirror substrate blank 1. This surface is to come to rest at a distance of about 19 to 22 m from the current surface 2 of the blank 1. The arcuate area for the intended final mirror grinding 10 is shown in FIGS. 2a and 2b by hatching in the side view of the mirror substrate blank 1. In the specific case, it is enough to remove a surface layer by grinding off 4 mm, whereby the bubble defect 6.1 originally positioned at a depth of 3 millimeters is eliminated. The two other bubbles 6.2 and 6.3 at an original depth of 18 mm and 21 mm, respectively, are shifted by removal of 4 mm in their depth position towards the new surface 21, where they are not detrimental to the intended final concave mirror polish or where they are also eliminated when the concave mirror grinding 10 is applied. The blank 11, as shown in FIG. 2b, which is reduced by 4 mm in its thickness, is suited for delivery to the optical manufacturer of EUV lithography devices.

EXAMPLE 2

A further silica glass blank 1 doped with 8 wt. % $TiO_2$, as described in Example 1, is face ground, but the visible polish is dispensed with. The mean roughness Ra of the face ground surface is thus 1.2 µm. Subsequently, the surface 2 is wetted over the whole area with immersion oil that has about the same refractive index as the Ti-doped silica glass. The immersion oil compensates for the roughness, so that the scattered light 5 from defects 6 can be easily resolved. The silica glass blank 1 prepared in this manner is mounted on a measurement table which is connected to a movable assembly, consisting of a laser light source 7 and a light detection element 8, which is part of a camera system with evaluation unit. The laser light 3 is equipped with a line focus, so that a line with the length 100 mm is directed at an angle of incidence α of 25° to the surface 2 of the blank 1. A laser with the rated power of 50 mW and a wavelength of 532 nm is used. The light detection element 8 in the camera system is oriented vertically towards the surface 2 of the blank 1 and serves as a detector for detecting the scattered light 5 emanating from the defect 6 in the blank. The light detection element 8 is formed by an infrared sensor. A scattered light 5 detected by the light detection element 8 at a distance x from the laser line yields a signal that is forwarded to the evaluation unit. The depth position T for the respective defect 6 is there calculated in accordance with the position data of the scattered light 5 and the laser light penetration point 4 by using the formula $T=x/(\tan(\arcsin(\sin(90-\alpha)/1.48))$. The value 1.48 stands for the refractive index of the Ti-doped silica glass blank.

Moreover, the scattered light 5 is detected in terms of its intensity and converted by the evaluation unit into a value for the diameter of the defect 6. For a fast and efficient detection of the defects 6, the 15" mirror glass blank 1 is scanned by grid-like movement of the penetration point 4 of the laser light 3 and the light detection element 8 over the whole surface 2 of the blank 1. Here, the laser line having a length of 100 mm moves vertically with respect to its line extension continuously (in the x-direction) over the surface 2 of the blank 1, wherein during the first measurement run the light detection element 8 is arranged at a minimal distance x of one millimeter from the line-shaped light penetration point 4 vertically above the surface 2 of the blank 1 and, in turn, moves in parallel with the laser line (y-direction) at a speed of about 25 mm/s. Potential bubble defects 6 located at a minimal depth of the surface layer are thereby detected. In further subsequent measurement runs in the x-direction over the same strip-like surface area, the light detection element 8 is spaced successively, in steps of 0.5 millimeters, from the light penetration point 4, so that due to repeated movement of the light penetration point 4 and the light detection element 8 over the surface or a sub-area of the surface, defects are progressively detected in increasingly deeper zones of the relevant surface layer. The 0.5 millimeter steps conform to a depth resolution of about 0.635 mm. In this case, the blank contains five bubbles, the positions of which are entered in Table 1. With the evaluation unit, it is also possible to obtain data on the bubble size. The size is between 40 μm and 280 μm. The position data of the bubbles are such that a surface layer of 5 mm must be removed for providing a mirror substrate blank for EUV lithography. Since one of the bubbles is positioned at the very edge at a depth of 12 mm, it is not detrimental to the final mirror grinding. Therefore, it is enough to remove an overdimension of 5 mm.

TABLE 1

| Example/ bubble no. | Position in T-direction [mm] | Measurement position x [mm] | Defect coordinates A/B from center of the blank [mm] | Size of the bubbles [μm] |
|---|---|---|---|---|
| 1/6.1 | 3 | 2.4 | 30/60 | estimated 200 |
| /6.2 | 18 | 14.4 | 20/100 | >100 |
| /6.3 | 21 | 16.8 | −120/−50 | >100 |
| 2 | 22 | 17.3 | 10/40 | 180 |
|  | 2 | 1.6 | 120/−100 | 150 |
|  | 12 | 9.5 | −170/30 | 280 |
|  | 10 | 7.8 | −100/−40 | 160 |
|  | 8 | 6.3 | −60/60 | 40 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for producing a colored mirror substrate blank (1; 11) of titanium-doped silica glass for EUV lithography with a thickness of at least 40 millimeters, the method comprising the steps of:
    a) face grinding a surface (2; 21) of the colored mirror substrate blank (1; 11) to form a face ground blank (1; 11);
    b) determining data on defects (6; 6.1; 6.2; 6.3) in a surface layer of the face ground blank (1; 11), wherein
        b1) light (3) penetrates at a place of the surface (2; 21) of the face ground blank (1; 11) at a predetermined angle α of less than 90° into the face ground blank (1; 11), the predetermined angle α being the angle between the light beam and a surface of the face ground blank (1; 11) as a horizontal,
        b2) the light (3) is scattered on the defects (6; 6.1; 6.2; 6.3) in the face ground blank, and
        b3) the scattered light (5) is detected at a distance x from a penetration point (4) on the surface (2; 21) of the face ground blank (1; 11) by a light detection element (8) which is vertically arranged thereabove;
    c) determining the position of the defects (6; 6.1; 6.2; 6.3) in the surface layer on the basis of the data obtained in method step b), a depth T at which the defect is positioned underneath the surface (2, 21) of the face ground blank (1; 11) being determined by the following formula:

$T=x/(\tan(\arcsin(\sin(90-\alpha)/n))$ n being the refractive index n of the titanium-doped silica glass; and
    d) partly or fully removing the surface layer in consideration of the determination of the position according to method step c) and with formation of the colored mirror substrate blank (1; 11).

2. The method according to claim 1, wherein the predetermined angle α at which the light (3) is incident on the surface (2; 21) of the face ground blank (1; 11) is set in the range of 5°-75°.

3. The method according to claim 1, wherein the light (3) is a laser light.

4. The method according to claim 3, wherein the laser light (3) is produced with a line focus, and wherein a laser with a rated power of at least 1 mW is used for producing the laser light.

5. The method according to claim 3, wherein a laser is selected which emits light in the wavelength range of 500-1500 nm.

6. The method according to any claim 1, wherein the light detection element (8) for detecting the scattered light (5) emanating from the defects (6; 6.1; 6.2; 6.3) in the colored mirror substrate blank (1; 11) is part of a camera system with an evaluation unit.

7. The method according to claim 6, wherein the camera system detects the intensity of the scattered light (5), and the size of the defects (6; 6.1; 6.2; 6.3) is arithmetically determined therefrom in the evaluation unit.

8. The method according to claim 1, wherein the face ground blank (1; 11) is wetted over its whole surface with an immersion oil prior to the determination of data on defects (6; 6.1; 6.2; 6.3) according to method step b).

9. The method according to claim 1, wherein the penetration point (4) and the light detection element (8) are guided in a grid-like manner over the surface (2; 21) of the face ground blank (1; 11).

10. A system for determining the position of defects (6; 6.1; 6.2; 67.3) in a colored mirror-substrate blank (1; 11) of titanium-doped silica glass for EUV lithography with a thickness of at least 40 millimeters in a method according to claim 1, the system comprising:
    a light source (7) and the light detection element (8) for the detection of the scattered light (5),
        wherein the light source (7) is arranged relative to the face ground blank (1; 11) such that the light (3) penetrates at the predetermined angle α of less than 90° into the surface (2; 21) of the face ground blank (1; 11),
        wherein the light is scattered on the defects (6; 6.1; 6.2; 6.3) in the face ground blank (1; 11),
        wherein the light detection element (8) is arranged such that it detects the scattered light (5) exiting at the distance x from the penetration point (4), vertically above the face ground surface (2; 21) of the blank, and wherein an evaluation unit determines the position of the defects (6; 6.1; 6.2; 6.3) on the basis of the data detected by the light detection element (8).

\* \* \* \* \*